United States Patent [19]

Ohkubo et al.

[11] Patent Number: 4,881,812
[45] Date of Patent: Nov. 21, 1989

[54] APPARATUS FOR DETERMINING BASE SEQUENCE

[75] Inventors: Kunihiko Ohkubo, Moriyama; Hidehiko Fujii, Kyoto, both of Japan

[73] Assignee: Shimadzu Corporation, Kyoto, Japan

[21] Appl. No.: 129,295

[22] Filed: Dec. 7, 1987

[30] Foreign Application Priority Data

Mar. 31, 1987 [JP] Japan ................................. 62-80390

[51] Int. Cl.[4] ...................... B01D 57/02; G01N 27/26
[52] U.S. Cl. ................................ 356/344; 204/299 R; 356/417
[58] Field of Search ....................... 356/344, 417, 431; 250/461.2, 563; 204/299 R, 182.8

[56] References Cited

U.S. PATENT DOCUMENTS

| | | | |
|---|---|---|---|
| 3,988,068 | 10/1976 | Sprague | 356/124 |
| 4,155,012 | 5/1979 | Clarke et al. | 250/563 |
| 4,277,178 | 7/1981 | Cushing et al. | 356/431 |
| 4,675,095 | 6/1987 | Kambara et al. | 204/182.8 |
| 4,703,182 | 10/1987 | Kroneis et al. | 250/461.2 |

OTHER PUBLICATIONS

*The Procedure of the National Academy of Science* (U.S.A.), vol. 74, p. 5463, (1977).
*High Technology,* Dec. 1986, (described at page 2 of the specification).
*The Hikari Gijyutsu Oyo System,* (Technology Application Systems), pp. 107–110, edited by the Japanese Precision Mechanical Society and Published by Shoko-bo in 1983.

Primary Examiner—Richard A. Rosenberger
Attorney, Agent, or Firm—Sandler & Greenblum

[57] ABSTRACT

An apparatus for determining a base sequence comprising an assembly for making an exciting beam incident on a slab of electrophoretic gel in a direction normal to the plane thereof, the gel containing nucleic acid fragments labeled with a labeling pigment and developed or being developed therein by electrophoresis, and a light receiving unit for receiving at an end face of the gel the luminescent emitted by the labeling pigment on the fragments developed in the gel.

10 Claims, 6 Drawing Sheets

APPARATUS FOR DETERMINING BASE SEQUENCE

BACKGROUND OF THE INVENTION

1. Field of the Invention

The present invention relates to an apparatus for determining the base sequences of nucleic acids according to the Sanger method by labeling primers with a pigment such as a fluorescent substance or phosphorescent substance first and spectroscopically reading the sequence from fragments as electrophoresed on a gel in the final step utilizing the luminescence from the labeling pigment.

2. Description of the Prior Art

The bands of nucleic acid fragments as developed by gel electrophoresis can be read utilizing fluorescence by two systems, i.e. on-line system and off-line system.

With the on-line system, nucleic acid fragments are electrophoresed on a gel, and during the electrophoresis, variations with time in the intensity of fluorescence of a point on the lane are read. With the off-line system, a gel of electrophoresed fragments is mounted after electrophoresis on a specific reading device to read the electrophoretic pattern.

According to the Sanger method (see Proc. Natl. Acad. Sci. U.S.A., vol. 74, p. 5463(1977)), four kinds of nucleic acid fragments wherein the terminal base is A (adenine), G (guanine), T (thymine) or C (cytosine) are used as a set of samples. When it is attempted to electrophorese on one lane one kind of sample having one of the four kinds of terminal bases, or to electrophorese many samples at the same time, the off-line system must measure the fluorescence of a slab of electrophoretic gel in two-dimensional directions, while even the on-line system requires one-dimensional high-speed fluorescence measurement in the direction of arrangement of the samples on the electrophoretic gel.

The known fluorescence measuring devices for slabs of electrophoretic gel are all of the on-line type.

Fluorescence measurement can be realized most simply using the apparatus shown in FIG. 9. (The apparatus described in "High Technology," December 1986, page 49 also belongs to this category.)

With reference to FIG. 9, a polyacrylamide gel 2 is immersed at its opposite ends in an electrolyte in electrode tanks 4 and 6. A voltage is applied across the electrode tanks 4, 6 from a power supply 8. One end of the gel 2 is formed with slots 10 for the injection of samples. Samples of different terminal bases are injected into the slots 10. The voltage applied from the power supply 8 electrophoreses the samples through the gel 2 in the direction of arrow 12 for development.

A laser 14 serving as an excitation light source emits an exciting beam, which is reflected at a half mirror or dichroic mirror 16 and projected on the gel 2 through an objective lens 18. The fluorescence from the fluorescent label on the sample migrating through the gel 2 is collected by the objective lens 18 again, transmitted through the half mirror or dichroic mirror 16 and then through a fluorescence selecting interference filter 20, impinges on a photomultiplier tube 22 serving as a photoelectric device and is thereby detected.

With the apparatus of FIG. 9, the single objective lens 18 is used both for projecting the exciting beam and for receiving the fluorescence, and the gel 2 is mechanically scanned with the overall optical system including the objective lens 18 and the components associated therewith in the direction 23 of arrangement of the samples (i.e. in a transverse direction perpendicular to the direction 12 of electrophoresis in the illustrated case).

FIG. 10 shows another apparatus for measuring the fluorescence of a slab of electrophoretic gel 2 (see the Proceeding of 24th Annual Meeting of the Japanese Biophysical Society in Japan, 3E 1130, October, 1986).

The exciting beam from a laser 14 serving as an excitation light source is made to incident by a condenser lens 24 on an end face of the gel 2 in a direction parallel to the gel. The fluorescence is received through a lens 26 one-dimensionally or two-dimensionally at once in a direction normal to the plane of the gel 2, passed through a fluorescence selecting interference filter 20, amplified by an image intensifier 28 and made to incident on a one- or two-dimensional photosensor (array type sensor) 30 for detection.

The apparatus of FIG. 9 for determining base sequences is adapted to measure the fluorescence in the direction of reflection of the exciting beam, so that Rayleigh scattering of the exciting beam provides intense background light to result in an impaired S-N ratio. Rayleigh scattering occurs intensely toward the front and rear but diminishes in a direction at an angle of 90 degrees with the exciting beam.

Further with the apparatus of FIG. 9, the objective lens 18, as well as the excitation optical system and the light-receiving optical system must be mechanically moved wholly or partly for scanning. For on-line measurement, it is required that all the lanes be scanned within a period of time which is sufficiently short relative to the speed of electrophoresis, whereas such a precision optical system is generally heavy, great in inertia and in no way adapted for high-speed scanning. Even if so adapted, the system will then be very costly.

In the case of the apparatus of FIG. 10, the electrophoretic gel 2 is exceedingly great relative to the diameter of the fluorescence receiving lens 26 which is usually usable, with the result that the solid angle of the fluorescence received is extremely small, giving a feeble fluorescence detection signal, which must be compensated for by using a one- or two-dimensional sensor and amplifying the output greatly. For this purpose, there arises a need to use, for example, the image intensifier 28, which nevertheless is very expensive.

Further if the gel 2 is thin, it is likely that the laser beam will not be confined in the gel. Another problem is also encountered in that unless the gel is accurately planar, the exciting beam will be bent upon incidence thereon, failing to afford any measurement.

SUMMARY OF THE INVENTION

The main object of the invention is to overcome the foregoing problems and to provide an apparatus for determining a base sequence wherein the luminescence from a labeling pigment is received from a direction at an angle of 90 degrees with an exciting beam in which direction the influence of scattering of the beam is diminished, without the necessity of using a light receiving unit which itself needs to be moved or of using any array-type sensor.

The invention provides an apparatus for determining a base sequence comprising an assembly for making an exciting beam incident on a slab of electrophoretic gel in a direction normal to the plane thereof, the gel containing nucleic acid fragments labeled with a labeling pigment and developed or being developed therein by electrophoresis, and a light receiving unit for receiving at an end face of the gel the luminescence emitted by the labeling pigment on the fragments developed in the gel.

With this apparatus, an exciting beam is made incident on a slab of electrophoretic gel in a direction normal to the plane thereof, the gel containing nucleic acid fragments labeled with a labeling pigment, such as a fluorescent substance, and developed or being developed therein by electrophoresis. The labeling pigment on the nucleic acid fragments developed in the gel emits fluorescence, which is propagated through the gel by total reflection and emerges from an end face of the gel. The emergent fluorescence is detected at the end face for the determination of the base sequence of the fragments.

The gel material to be used in the invention for developing nucleic acid fragments is one which is usually used for the Sanger method, for example, 8% polyacrylamide gel.

Examples of useful exciting beams are laser beams, among which argon laser beam is desirable.

The primers of nucleic acid to be used in the invention for the determination are labeled with a labeling pigment before use. Examples of useful labeling pigments are as follows.

| Name (symbol) | Max. absorption wavelength (nm) | Exciting Ar laser wavelength (nm) | Max. wavelength of fluorescence emitted (nm) |
|---|---|---|---|
| Fluoresein isothiocyanate (FiTC) | 489 | 488 | 520 |
| Tetramethyl rhodamine isothiocyanate (TRiTC) | 554 | 514 | 573 |
| 4-Fluoro-7-nitrobenzofurazen (NBD-F) | 475 | 488 | 540 |

According to the present invention, the exciting beam is made incident on a slab of electrophoretic gel in a direction normal to the plane of the gel. The means therefor can be one selected from among those known for use in the art.

When the exciting beam is to be made incident on an electrophoretic gel which has already been developed by electrophoresis, incidence means is used for scanning the gel in the direction of electrophoresis and in a direction perpendicular to this direction. An example of such means is one including a pair of galvanomirrors. Further when an electrophoretic gel being developed by electrophoresis is to be handled, means is used which is adapted to scan the gel along a straight line perpendicular to the direction of electrophoresis, such as one incorporating a regular polyhedral mirror and an fθ lens system.

The fluorescence emitted by the labeled nucleic acid fragment exposed to the exciting beam is propagated through the gel by total reflection and emerges from an end face of the gel, so that the emergent fluorescence is received at the end face for detection. The fluorescence is received by a unit which comprises a plurality of optical fibers in the form of a bundle. This bundle has a rectangular end face of a small width and conforming to the shape of the end face of the gel. The other end face of the bundle is opposed to the sensitive surface of a photoelectric device. The light receiving unit may be in the form of a molded product prepared by molding the bundle of optical fibers into a desired shape using glass, acrylic resin or the like.

The fluorescence emerging from the end face of the light receiving unit is passed, for example, through a fluorescence selecting interference filter first and then converted to an electric signal by a photomutiplier tube. The signal is further converted by an A/D converter to a digital signal, which is fed to a computer. On the other hand, data representing the position of incidence of the exciting beam is fed from a beam position sensor to the microcomputer. In this way, the base sequence of the DNA checked is determined.

The intensity of the fluorescence emitted from the location of projection of the exciting beam and emergent from the end face of the electrophoretic gel is thought to be dependent on the solid angle as the light is seen at the gel end face and actually varies with the condition of the end face, etc. Accordingly, the intensity of the fluorescence appearing at the end face can be corrected by actual measurements to assure determination with improved accuracy. The apparatus of the invention may be provided with a device for effecting such correction. Such a device would, for example, have a means for receiving an input expressed as the intensity of the singal of the photomultiplier tube and an input expressed as the intensity of fluorescence at the position of projection of the exciting beam to correct the intensity of fluorescence on an experimental basis. The DNA base sequence is determined according to the intensity of fluorescence thus corrected.

To utilize the fluorescence with improved efficiency and to measure the intensity thereof with higher sensitivity by intensifying the exciting beam, it is useful according to the invention to cover with a mirror or like reflector at least one of the end faces, front surface and rear surface of the electrophoretic gel other than the measuring end face of the gel and the surface portion thereof to be exposed to the exciting beam.

For example, when an electrophoretic gel already developed is to be scanned over a surface in its entirety, the reflector may be provided over the entire surface opposite to the surface to be exposed to the exciting beam and over the end face opposite to the end face where the light receiving unit is disposed. Further when an electrophoretic gel being developed is to be scanned along a straight line perpendicular to the direction of electrophoresis, the reflector may be provided over all the surfaces of the gel other than the measuring end face thereof and the striplike portion to be exposed to the exciting beam.

The apparatus of the invention for use in determining the base sequences of nucleic acids will be usable for other purposes, for example, for the fluorescence determination of usual electrophoretic gels and thin layer chromatography.

DESCRIPTION OF THE PREFERRED EMBODIMENTS

Figure 1:
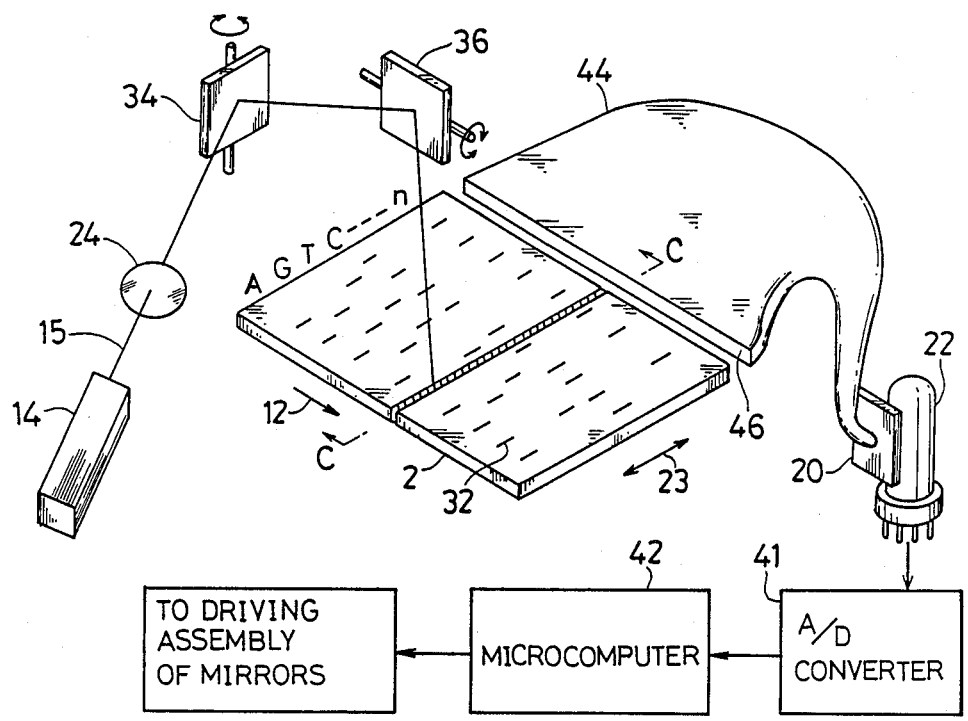
FIG. 1 is a perspective view schematically showing an embodiment.

The present invention will be described below with reference to the embodiments shown in the drawings. However, these embodiments in no way limit the invention.

Figure 2:
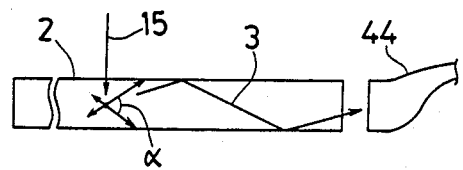
FIG. 2 is a schematic view in section taken along the line C—C in FIG. 1.

FIG. 1 shows a base sequence determining apparatus of the off-line type embodying the invention, and FIG. 2 is a view in section taken along the line C—C in FIG. 1.

Indicated at 2 is an electrophoretic polyacrylamide gel prepared according to the Sanger method by labeling DNA fragment primers with FiTC (listed above), injecting the samples individually in the order of the terminal bases A, G, T and C into one end of the gel 2 and electrophoresing the samples by an electrophoretic apparatus. Indicated at 32 are DNA fragments developed by the electrophoresis.

An argon laser 14 serving as an excitation light source emits an exciting beam 15, which is concentrated by a condenser lens 24. The argon laser emits a beam at 488 nm. Indicated at 34 is a galvanomirror for scanning the surface of the gel 2 with the beam 15 in the direction 12 of electrophoresis. The exciting beam 15 reflected from the galvanomirror 34 is directed by a galvanomirror 36 toward the gel 2 to scan the surface of the gel at a high speed in a zone direction 23 perpendicular to the direction 12. The angles of rotation of the mirrors 34 and 36 are fed to a microcomputer 42 as data representing the position of projection of the exciting beam on the gel 2. These mirrors 34 and 36 are rotated by drive means (not shown) in response to signals from the microcomputer 42.

A bundle of optical fibers 44 is provided at one side of the gel 2. The optical fibers are so arranged into the bundle 44 that the bundle has a rectangular end face with a small width and shaped in conformity with the shape of an end face of the gel 2 to which it is opposed. The other end of the bundle 44 is small-sized. The light emanating from this end face is led through a fluorescence selecting interference filter 20 to a photomultiplier tube 22. The detection signal from the tube 22 is converted by an A/D converter 41 to a digital signal, which is then fed to the microcomputer 42.

The microcomputer 42 receives from the galvanomirrors 34, 36 the signals representing the beam projection position on the gel 2 and accepts the fluorescence at this position in terms of the detection signal from the photomultiplier tube 22. In this way, by scanning the entire surface of the gel 2 by the galvanomirrors 34, 36, the pattern of the DNA fragment samples developed on the gel 2 by electrophoresis can be obtained as the fluorescence detection signal from the tube 22.

When the exciting beam 15 is projected on the DNA fragment sample developed in the gel 2, fluorescence 3 occurs as shown in FIG. 2.

We have conducted experiments and research and found that when a DNA fragment labeled with a fluorescent substance is present at the position where the exciting beam impinges on the gel, the fluorescence emitted by the substance is propagated through the gel by total reflection and emerges from an end face of the gel. The emergent fluorescence is due to total reflection because even if the gel end face is viewed at widely varying angles, the fluorescence is observable and further because the fluorescence is still observable even if the gel is bent. Since the light detected at the end face of the gel is transmitted by total reflection, the solid angle, in the direction of thickness of gel, of the light which can reach the end face is dependent on the total reflection critical angle of the gel and of the neighboring optical material) and is very great. (The solid angle is indicated at α in FIG. 2.) Furthermore, the direction from which the fluorescence is received is at an angle of 90 degrees with the exciting beam, and in this direction, the propagation of Rayleigh scattered light is minimized. Our experiments have revealed that it was totally unlikely that the exciting beam would scatter in directions within the plane of the electrophoretic gel, propagate and excite the fluorescent substance at locations where no exciting beam was projected.

The attenuation of the fluorescence due to the scattering of light in the gel 2 at this time is as slight as about 3%, as measured using 8% polyacrylamide gel generally used in the Sanger method.

The fluorescence emergent at the end face is received by the optical fiber bundle 44, propagated through the bundle 44 and through the fluorescence selecting interference filter 20 and converted to an electric signal in the photomultiplier tube 22. The optical fiber bundle 44 to be used is, for example, ESKA (commercial product of Mitsubishi Rayon Co., Ltd.).

As well known, the DNA fragments in the present case have already been developed (i.e., separated) by electrophoresis in the order of decreasing length in the migration direction of electrophoresis, so that the sequence can be determined by reading the pattern from zone to zone (as grouped by the difference in the terminal base). From the angles of rotation of the galvanomirrors 34, 36, the location where the exciting beam impinges is calculated by the microcomputer 42, and the intensity of fluorescence then emitted is detectable, revealing an electrophoretic pattern as contemplated.

Figure 3:
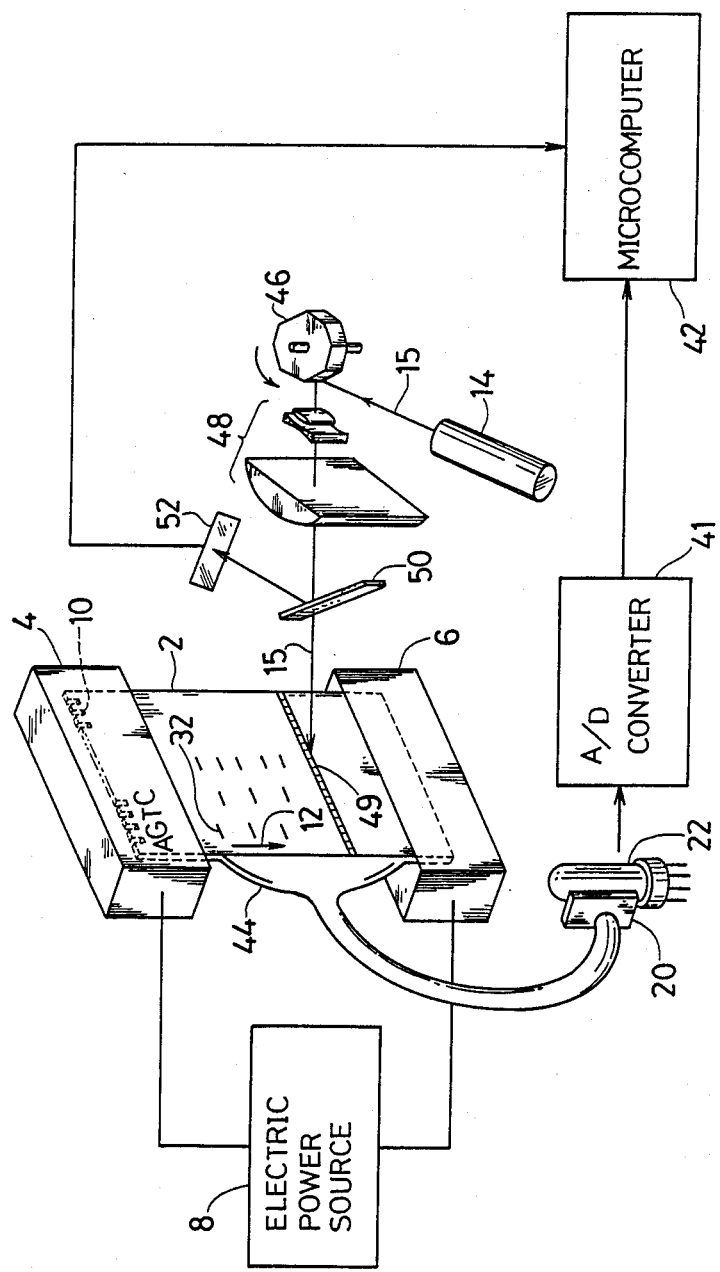
FIG. 3 is a perspective view schematically showing another embodiment.

FIG. 3 shows a base sequence determining apparatus of the on-line type embodying the invention.

An electrophoretic polyacrylamide gel 2 is placed at its opposite ends in electrode tanks 4, 6, with a voltage applied across the tanks by a power supply 8. DNA fragments prepared by the Sanger method already described and having primers labeled with FiTC are injected into slots 10 at one end of the gel 2 in the order of terminal bases A, G, T and C. The fragments are electrophoresed as bands 32 by the application of the voltage. An argon laser 14 emits an exciting beam 15 at 488 nm. Indicated at 46 is a regular polyhedral mirror for projecting the exciting beam 15 along a straight line for scanning. An fθ lens system 48 converges the beam 15 on the straight line. The mirror 46 and the fθ lens system 48 cause a spot of the exciting beam 15 to scan the gel 2 on the straight line 49 perpendicular to the direction 12 of electrophoresis at a high speed. The scanning of a plane by such regular polyhedral mirror and fθ lens system is well known (see for example, "Hikari Gijyutsu Oyo System (Technology Application Systems)" pages 107 to 110 edited by the Japanese Precision Mechanical Society, published by Shoko-do, in 1983).

A half mirror 50 is disposed in the optical path between the fθ lens system 48 and the gel 2. The exciting beam 15 is partially reflected from the half mirror 50 for a beam position sensor 52 to detect the position of the beam 15. For example, S-1352 (product of Hamamatsu Photonics Inc., Hamamatsu, Japan) can be used as the sensor 52.

The same optical fiber bundle 44 as shown in FIG. 1 is disposed with its rectangular end face opposed to an end face of the gel 2. The other end of the bundle 44 is opposed to a photomultiplier tube 22 with a fluorescence selecting interference filter 20 interposed therebetween.

The detection signal from the photomultiplier tube 22 is converted by an A/D converter 41 to a digital signal, which is then fed to a microcomputer 42. The microcomputer 42 also receives from the sensor 52 data indicating the position of projection of the exciting beam 15.

The operation of the embodiment of FIG. 3 will now be described.

When there is a band of DNA fragment at the position of projection of the exciting beam 15 at a certain moment, the band emits fluorescence, which is propagated through the electrophoretic gel 2 and incident on the optical fiber bundle 44. The light then impinges on the photomultiplier tube 22 through the interference filter 20 as already described. The band pattern of the DNA is detected by the microcomputer 42 from the data given by the sensor 52 and indicating the position of projection of the beam 15 and the fluorescence detection signal from the tube 22. Since the DNA fragments are developed in the order of decreasing molecular length in the direction of electrophoresis as already mentioned, the base sequence can be determined from the detected pattern by a well-known method.

Figure 4:
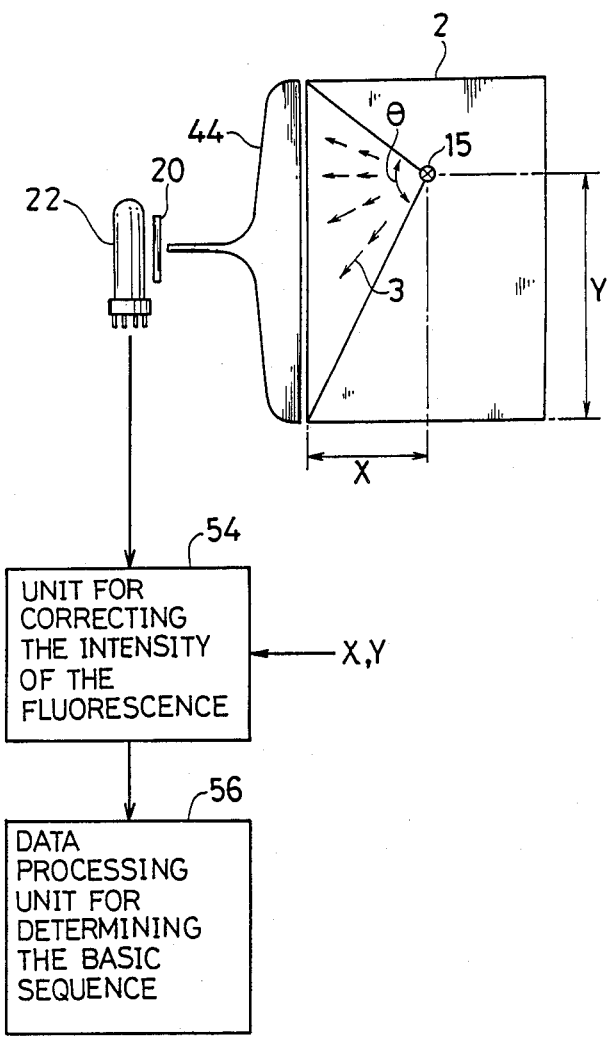
FIG. 4 is a schematic plan view showing another embodiment.

FIG. 4 shows another embodiment which is adapted to correct the intensity of fluorescence emitted from the position of projection of an exciting beam 15 and emanating from an end face of an electrophoretic gel 2.

It is thought that the intensity of the fluorescence 3 reaching the end face of the gel 2 is dependent on the solid angle θ through which the gel end face is viewed from the position of projection of the exciting beam 15. In actuality, however, the intensity varies, for example, with the condition of the end face. Accordingly, the intensity of the fluorescence emerging from the end face is corrected with the intensity of the fluorescence 3 measured at the position (X, Y) where the beam 15 is incident on the gel. Indicated at 54 is a unit for carrying out calculation for intensity correction. The intensity of the signal from a photomultiplier tube 22 and the intensity of fluorescence at the position (X, Y) are fed to this unit to correct the intensity of fluorescence at the gel end face on an experimental basis. A data processing unit 56 determines the base sequence of DNA based on the corrected fluorescence intensity.

Figure 5:
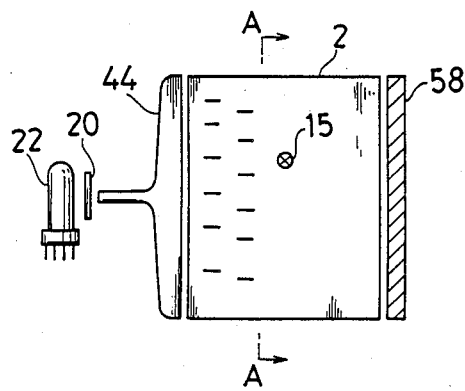
FIG. 5 is a schematic plan view showing another embodiment.
Figure 6:
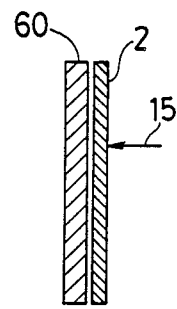
FIG. 6 is a view in section taken along the line A—A in FIG. 5.

FIG. 5 is a schematic plan view showing another embodiment, and FIG. 6 is a view in section taken along the line A—A in FIG. 5.

With the embodiment of FIG. 5, an exciting beam 15 is projected on a gel 2 from the front toward the rear side perpendicular to the plane of the drawing.

An optical fiber bundle 44 is disposed at one end face of the gel 2, and a mirror 58 at the other end face thereof, whereby the fluorescence propagated in a direction away from the fiber bundle 44 is reflected at the mirror 58 and directed toward the bundle 44.

A mirror 60 for reflecting the exciting beam 15 is also provided as opposed to the rear surface of the gel 2 opposite to the other surface thereof to be exposed to the beam 15.

The mirror 58 serves to utilize the fluorescence efficiently, while the mirror 60 intensifies the exciting beam 15, hence improved sensitivity.

Figure 7:
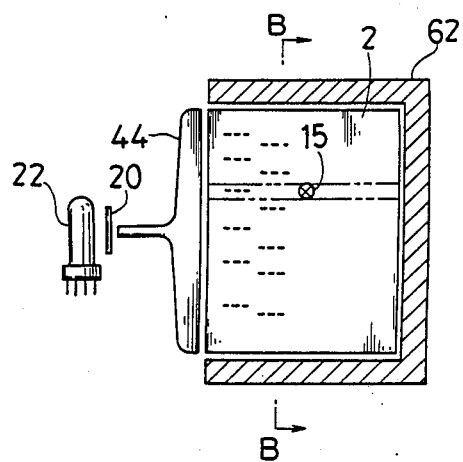
FIG. 7 is a schematic plan view showing another embodiment.
Figure 8:
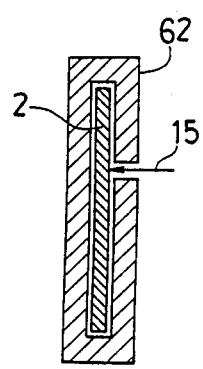
FIG. 8 is a view in section taken along the line B—B in FIG. 7.
Figure 9:
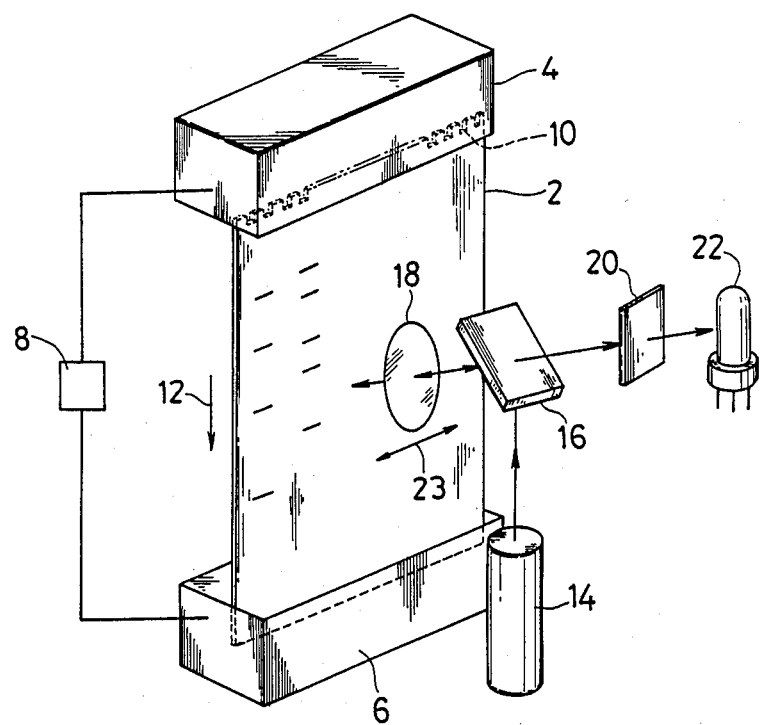
FIGS. 9 and 10 are perspective views schematically showing different conventional apparatus for determining base sequences.

FIGS. 7 and 8 show another embodiment of the invention designed as an on-line system. FIG. 8 is a view in section taken along the line B—B in FIG. 7.

With this embodiment, an electrophoretic gel 2 is covered with a mirror 62 except at an end face thereof provided with a fluorescence receiving bundle 44 of optical fibers and at a small area where the gel is scanned with an incident exciting beam 15.

The mirror 62 covering the gel enables the apparatus to utilize the fluorescence and exciting beam 15 with a further improved efficiency and to exhibit increased sensitivity.

The foregoing embodiments include a bundle 44 of optical fibers as means for receiving fluorescence from an end face of the electrophoretic gel 2. Since the light receiving means is used merely for guiding the fluorescence from the gel end face to the sensitive surface of a photoelectric device, some other means, such as a molded optical product, is usable insofar as such means performs the above function.

Although a fluorescent substance is used as a labeling pigment for the above embodiments, a phosphorescent substance is alternatively usable (see Japanese patent application SHO 62-2230).

With the base sequence determining apparatus of the invention, a slab of electrophoretic gel having nucleic acid fragments developed therein is exposed to an exciting beam projected thereto in the direction of thickness of the gel, and the luminescence emitted by a labeling pigment on the fragments is received at the end face of the gel. Consequently, the luminescence can be received from a direction at an angle of 90 degrees with the exciting beam in which direction Rayleigh scattering of the beam very objectionable to the measurement of the luminescence is minimum.

Since the position of measurement is specified by the location where the exciting beam is incident, there is no need to receive the light from a particular location as distinguished as such. This obviates the need for an image forming lens, assures a great solid angle, results in a higher S-N ratio, eliminates the need for an expensive one- or two-dimensional array type sensor of high sensitivity and ensures the measurement with use of one photomultiplier tube or like photoelectric device. The light receiving assembly is therefore available at about 1/100 the conventional cost.

Figure 10:
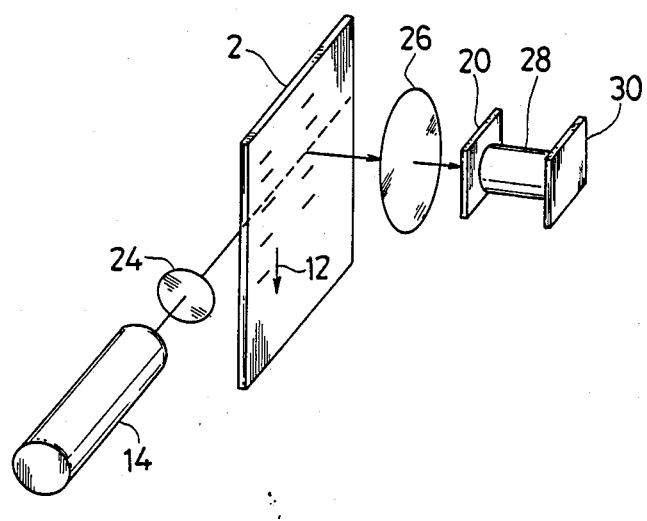

Unlike the apparatus of FIG. 10, the present apparatus is so adapted that the fluorescence is propagated through the electrophoretic gel. Consequently, no problem arises even if the gel is thin.

The fluorescence is slightly greater than the exciting beam in wavelength and is less susceptible than the beam to Rayleigh scattering due to the gel.

Since the fluorescence is propagated by total reflection for detection, the deformation or distortion of the gel poses no problem unlike the apparatus of FIG. 10.

Thus, base sequences can be determined accurately with high sensitivity using the apparatus of the invention.

What is claimed is:

1. An apparatus for determining a base sequence comprising an assembly for making an exciting beam incident on a surface of a slab of electrophoretic gel in a direction normal to said surface, the gel containing nucleic acid fragments labeled with a labeling pigment and developed or being developed therein by electrophoresis; means for concentrating said exciting beam on said gel; means for scanning said surface of said gel with said exciting beam; and a light receiving unit for receiving at an end face of said gel the luminescence emitted by said labeling pigment on the fragments developed in said gel.

2. An apparatus as defined in claim 1 wherein the light receiving unit comprises a bundle of optical fibers having one end face in the form of a rectangle of small width and shaped in conformity with the shape of said end face of the gel and the other end face opposed to the sensitive surface of a photoelectric device.

3. An apparatus as defined in claim 1 wherein the light receiving unit comprises a shaped optical product having one end face in the form of a rectangle of small width and shaped in conformity with the shape of said end face of the gel and the other end face opposed to the sensitive surface of a photoelectric device.

4. An apparatus as defined in claim 1 which comprises means for correcting the intensity of the received luminescence at the position of incidence of the exciting beam.

5. An apparatus as defined in claim 1 wherein the gel is covered with a reflecting mirror over at least one of the end faces, front surface and rear surface thereof other than said end face of the gel and the front surface portion thereof to be exposed to the exciting beam.

6. An apparatus for determining a base sequence comprising an assembly for making an exciting beam incident on a slab of electrophoretic gel in a direction normal to the plane thereof, the gel containing nucleic acid fragments labeled with a labeling pigment and developed or being developed therein by electrophoresis, and a light receiving unit for receiving at an end face of the gel the luminescence emitted by the labeling pigment on the fragments developed in the gel, wherein the incidence assembly comprises an excitation light source, a condenser lens for concentrating an exciting beam from the light source, and means for making the concentrated exciting beam incident on the gel having the fragments developed therein by electrophoresis in a direction normal to the plane of the slab of gel and for scanning the surface of the gel with the beam in the direction of electrophoresis and in a direction perpendicular thereto.

7. An apparatus for determining a base sequence comprising an assembly for making an exciting beam incident on a slab of electrophoretic gel in a direction normal to the plane thereof, the gel containing nucleic acid fragments labeled with a labeling pigment and developed or being developed therein by electrophoresis, and a light receiving unit for receiving at an end face of the gel the luminescence emitted by the labeling pigment on the fragments developed in the gel, wherein the incidence assembly comprises an excitation light source, and means for concentrating an exciting beam from the light source, making the concentrated exciting beam incident on the gel having the fragments being developed therein by electrophoresis in a direction normal to the plane of the slab of gel and scanning the surface of the gel with the beam on a straight line perpendicular to the direction of electrophoresis.

8. An apparatus for determining a base sequence, comprising an assembly for making an exciting beam of laser light incident on a surface of a slab of electrophoretic gel in a direction normal to the plane of said surface, said gel containing nucleic acid fragments labeled with a labeling pigment and developed or being developed therein by electrophoresis; means for scanning the surface of said gel with said exciting beam; and a light receiving unit for receiving, at an end face of said gel, luminescence emitted by said labeling pigment on said fragments developed in said gel.

9. The apparatus as defined in claim 8, further comprising means for condensing said exciting beam on said gel.

10. The apparatus as defined by claim 8, wherein said exciting beam of laser light is an argon laser beam.

* * * * *